United States Patent [19]
Greene et al.

[11] Patent Number: 5,334,702
[45] Date of Patent: Aug. 2, 1994

[54] COMPOSITIONS WHICH ARE IMMUNOLOGICALLY CROSSREACTIVE WITH ANTIBODIES AND PREPARATIVE METHODS THEREFOR

[75] Inventors: Mark I. Greene, Penn Valley; Horacio U. Saragovi, Philadelphia, both of Pa.; Michael Kahn, Chicago, Ill.

[73] Assignees: University of Illinois, Champaign, Ill.; Trustees of the University of Pennsylvania, Philadelphia, Pa.

[21] Appl. No.: 933,013

[22] Filed: Aug. 20, 1992

Related U.S. Application Data

[63] Continuation-in-part of Ser. No. 674,866, Mar. 25, 1991, abandoned, and Ser. No. 703,465, May 21, 1991, abandoned.

[51] Int. Cl.$^5$ .......................... C07K 7/02; C07K 7/50; C07D 245/00
[52] U.S. Cl. .................................. 530/323; 530/317; 530/332; 530/345; 530/387.1; 540/460; 364/496
[58] Field of Search ............ 530/332, 323, 317, 387.1, 530/345; 514/183, 19, 18; 540/460; 364/496; 424/88

[56] References Cited

U.S. PATENT DOCUMENTS 2,156,300 5/1939 Lippert et al. ...................... 540/460
4,939,666 7/1990 Hardman ............................ 364/496
4,946,778 8/1990 Ladner et al. ...................... 435/69.6

OTHER PUBLICATIONS

Kieber–Emmons et al (1987) Intern. Rev. Immunol. 2: 339–356.
Williams et al (1989) PNAS 86: 5537–5541.
Jones et al (1986) Nature 321: 522–525.
Kahn et al (1988) "The Design and Synthesis of Mimetics of Peptide β–Turns" J. Molecular Recognition 1(2): 75–79.
Ball et al (1990) "Conformational Constraints: Nonpeptide β–turn Mimics" J. Molecular Recognition 3(2): 55–64.
Morgan et al "Approaches to the Discovery of Non-Peptide Ligands for Peptide Receptors and Peptidases" Vinick et al eds, Annual Reports in Medicinal Chemistry vol. 24, pp. 243–252, 1989 Academic Press, Inc.
Kahn et al (1986) "The Design and Synthesis of a Non Peptide Mimic of an Immunosuppressing Peptide" Tetrahedron Lett. 27(4): 4841–4844.
Kahn et al (1987) "The Design and Synthesis of a Nonpeptide Mimic of Erabutoxin" Heterocycles 25:29–31.
Kahn et al (1987) "Methodology for the Synthesis of Numetics of Peptide β–Turns" Tetrahedron Lett 28(15): 1623–1626.

(List continued on next page.)

Primary Examiner—Kay K. Kim
Attorney, Agent, or Firm—Woodcock, Washburn, Kurtz, Mackiewicz & Norris

[57] ABSTRACT

Compositions which are immunologically crossreactive with antibodies are provided, together with preparative and therapeutic methods therefor. The compositions preferably comprise a plurality of covalently bound synthetic compounds, at least one of which is individually crossreactive with at least one complementarity determining region (CDR) of the antibody. Preferred processes for preparing the immunologically crossreactive compounds comprise identifying chemical functionality such as hydroxyl groups in the CDR which participates in at least one immunological binding phenomena, determining the three-dimensional positioning of the chemical functionality, and synthesizing a compound which comprises substantially the same chemical functionality as the CDR and which has at least one conformation wherein the three-dimensional positioning of the chemical functionality is substantially identical to the three-dimensional positioning of the chemical functionality of the CDR.

1 Claim, 7 Drawing Sheets

OTHER PUBLICATIONS

Kahn et al (1988) "Nonpeptide Mimetics of β-Turns: A Facile Oxidative Intramolecular Cycloaddition of an Azodicarbonyl System" J. Am. Chem. Soc. 110: 1638–1639.

Freidinger et al (1980) "Bioactive Conformation of Luteinizin Hormone–Releasing Hormone: Evidence from a Conformationally–Constrained Analog" Science 210: 656–658.

Valle et al (1989) "Crystal–State Structural Analysis of Two γ–Lactam–Restricted Analogs of Pro–Leu–Gly–NH$_2$" Int. J. Peptide Protein Res. 33: 181–190.

Kretenansky et al (1982) "A New Approach to Conformationally Restricted Peptide Analogs: Rigid β–Bends 1, Gnkepholin as an Example" Biochem. Biophys. Res. Commun. 109(4): 1368–1374.

Kemp et al (1988) "A Convenient Preparation of Derivatives of 3(s)–amino–10(R)–carboxy–1,6–diaza–cyclodeca–2,7–dione. The Dilactaim of L–α,–β–diaminobuty αc acid and D–Glutamic Acid: A β–Turn Template" Tetrahedron Lett 29(40): 5057–5060.

Hruby et al (1990) "Emerging Approaches in the Molecular Design of Receptor–Selective Peptide Ligands: Conformational, Topographical and Dynamic Considerations" Biochem J. 268: 249–262.

Fauchere (1986) "Elements for the Rational Design of Peptide Drugs" Adv. Drug Res 15: 29–69.

Arrhenius et al (1990) Proc. Am. Peptide Symp., Rivier and Marshall, Eds, ESCOM, Leiden 1990 pp. 870–872 "The Substitution of an Amide–Amide Backbone Hydrogen Bond in an α–Helical Peptide with a Covalent Hydrogen Bond Mimic".

Toniolo (1990) "Conformationally Restricted Peptides Through Short–Range Cyclizations" Int. J. Peptide Protein Res. 35: 287–300.

COMPOSITIONS WHICH ARE IMMUNOLOGICALLY CROSSREACTIVE WITH ANTIBODIES AND PREPARATIVE METHODS THEREFOR

GOVERNMENT SUPPORT

Portions of this invention were supported by National Science Foundation Grant DMV804861 and National Institute of Health Grants UI08191, NS16998, and GM38260.

This invention is a continuation-in-part of U.S. application Ser. No. 674,866 filed Mar. 25, 1991, now abandoned, and of U.S. application Ser. No. 703,465 filed May 21, 1991 now abandoned.

FIELD OF THE INVENTION

This invention relates to synthetic compositions which exhibit immunological crossreactivity with antibodies and, more particularly, to synthetic compounds which exhibit immunological crossreactivity with one or more antibody complementarity determining regions.

BACKGROUND OF THE INVENTION

Antibodies are a class of proteins produced by an organism in response to the invasion of foreign compounds called antigens. The antibodies produced characteristically bind to the antigens in a highly specific manner to initiate protection against infection or disease. The human body is capable of synthesizing more than a million different types of antibody molecules.

Each antibody or immunoglobulin molecule is composed of four polypeptide chains of two different kinds: a pair of identical high-molecular-weight chains, called "heavy" or "H" chains, and a pair of identical lower-molecular-weight chains called "light" or "L" chains. Each of the four polypeptide chains that form the monomeric immunoglobulin G (IgG) molecule is divided into separate regions called "domains." There are two domains in the L chains and four domains in the H chains. Within each of the domains, folding of the polypeptide chain produced two parallel planes, each containing several segments with folded beta structure. Among the IgG class, certain domains of both the H and L chains are homologous or constant and certain domains are variable. Each L chain has one variable and one constant domain; each H chain has one variable and three constant domains. The variable domains occur near the amino-terminus of the polypeptide chains and together create an antigen-binding site that is unique to that IgG molecule. The variable domain of each light chain is designated $V_L$ and the constant domain $C_L$. The variable domain of a heavy chain is designated $V_H$ and the constant regions $C_H1$, $C_H2$, $C_H3$.

At the level of primary amino acid sequence, each variable region of an antibody is composed of four framework regions interspersed with three hypervariable regions, also known as complimentarity determining regions (CDRs). The three-dimensional structure of the framework regions comprise an array of anti-parallel β-sheets, from which project loop-shaped CDRs. Differing patterns of loop sizes from one antibody to another establish the gross topography of variable regions, combining with the effect of amino acid sequence diversity to generate antibody specificities.

Studies in which antibodies have been co-crystallized with bound antigen indicate that the CDRs are involved in antigen binding. Recent studies using synthetic peptides derived from antibody CDRs confirm that these structures are involved in contacting the antigen, and indicate that the chemical nature of specific amino acids is critical in determining binding specificity.

Given their demonstrated reactivity, antibodies would appear to be quite useful in programs for the treatment of disease. However, successful clinical therapies involving the provision of antibodies produced outside the human body have yet to be successfully developed, despite the considerable progress which recently has been made in monoclonal production techniques. One significant impediment to antibody therapies is the fact that any given antibody is itself an antigen which elicits the production of antibodies to itself, called anti-idiotypic antibodies, through an immune response. It has been found, for example, that administering antibody-containing compositions frequently produces serum sickness or other side effects. Therapeutic approaches also are complicated by the basic chemical instability of most antibodies.

Recent advances in genetic engineering, immunoglobulin sequence analysis, x-ray crystallography, and computer-assisted molecular modeling have greatly facilitated the design of potentially improved antibodies. These technical advances have also spurred considerable research activity in compositions which react in the same manner as antibodies Vet which do not themselves elicit an immune response. Certain synthetic peptides derived from CDR sequences have been shown to possess properties which are similar to the intact antibody in that they can inhibit idiotype-antiidiotype interactions, bind specific antigens, interact with cellular receptors, and stimulate biological processes. For example, Williams, et al., Proc. Natl. Acad. Sci. U.S.A., 1989, 86, 5537, disclose that a biologically active peptide derived from the second complementarity region of the monoclonal antibody 87.92.6 light chain variable region can bind to the reovirus type 3 receptor and inhibit DNA synthesis in a manner similar to the antibody. Williams, et al. additionally identify specific amino acid residues and structural features involved in producing these effects, and suggest that short, nonimmunogenic peptides modeled after the hypervariable regions of antibodies may lead to the development of biologically active substances having clinical utility. However, clinical applications for such peptides are complicated by, for example, concerns of chemical instability, bioavailability, proteolytic degradation, and oral inactivity. In addition, peptides are generally not able to cross lipid membrane barriers such as the blood-brain barrier.

OBJECTS OF THE INVENTION

It is one object of the present invention to provide compositions which react with antigens and other receptors in a manner similar to antibodies.

It is another object of the invention to provide compositions which react in a manner similar to antibodies, yet which do not themselves elicit an immune response.

It is still another object of the invention to provide compositions comprising one or more synthetic compounds which react in a manner similar to the complementarity determining regions of the antibodies, together with methods for making such compounds.

It is a further object to provide compositions and compounds which are chemically more stable than natural antibodies or peptides derived therefrom.

It is still a further object to provide prophylactic, diagnostic, and therapeutic uses for synthetic compounds which react in a manner similar to the complementarity determining regions of the antibodies.

SUMMARY OF THE INVENTION

These and other objects are accomplished by the present invention, which provides compositions which are immunologically crossreactive with at least one antibody together with preparative and therapeutic methods therefor. The compositions of the invention preferably comprise a plurality of covalently bound synthetic compounds, at least one of which is individually crossreactive with at least one complementarity determining region (CDR) of an antibody. In preferred embodiments, where the CDR has a plurality of hydroxyl groups positioned in three-dimensional space, the synthetic compound comprises substantially the same number of hydroxyl groups and exists in at least one conformation wherein the three-dimensional positioning of its hydroxyl groups is substantially identical to the three-dimensional positioning of the hydroxyl groups of the CDR.

In some embodiments, the invention provides synthetic compounds which are immunologically crossreactive with the second CDR of the 87.92.6 monoclonal antibody (mAb). One preferred compound has the structure:

(1)

Preferred processes for preparing the immunologically crossreactive compounds of the invention comprise the steps of identifying chemical functionality such as hydroxyl groups in the CDR which participate in at least one immunological binding phenomena, determining the three-dimensional positioning of the chemical functionality, and synthesizing a compound which comprises substantially the same chemical functionality as the CDR and which has at ]east one conformation wherein the three-dimensional positioning of the chemical functionality is substantially identical to the three-dimensional positioning of the chemical functionality of the CDR. Preferably, chemical functionality which participates in binding is identified by preparing at least one variant peptide which has an amino acid sequence which differs from the amino acid sequence of the CDR by one or more amino acids and then comparing the activity of the variant peptide with the activity of the CDR for the immunological binding phenomena.

Preferred processes for preparing compounds which are immunologically crossreactive with antibody CDRs having a plurality of hydroxyl groups comprise the steps of determining the position in three-dimensional space of at least one hydroxyl group of the CDR and synthesizing a compound which comprises substantially the same number of hydroxyl groups as the CDR and which has at least one conformation wherein the three-dimensional positioning of its hydroxyl groups is substantially identical to the three-dimensional positioning of the hydroxyl groups of the CDR.

Also provided are methods for producing a prophylactic or therapeutic immune response in a mammal by administering to the mammal a composition comprising one or more of the synthetic, immunologically crossreactive compounds of the invention.

Compositions comprising relatively small synthetic compounds can now be developed in accordance with the invention to mediate the biological effects of antibodies or other ligands. These compounds should possess beneficial properties such as increased half-life, the ability to cross the blood-brain barrier, and lack of immunogenicity and thus should be useful for the development of new pharmaceutical, therapeutic, diagnostic, and receptor binding agents.

BRIEF DESCRIPTION OF THE DRAWINGS

The numerous objects and advantages of the present invention may be better understood by those skilled in the art by reference to the accompanying figures, in which:

FIG. 1 is a graph showing the manner in which a number of moieties immobilized on solid supports bind 9BG5 mAb.

FIG. 2 is a graph showing the manner in which two moieties inhibit the binding of 9BGSmAb to VLSH in solution.

FIG. 3 is a graph showing the manner in which a number of moieties affect the incorporation of $^3$H-Thymidine by ConA T cells.

FIG. 4 is a schematic diagram showing the synthetic pathway to azetidinone (10).

FIG. 5A, 5B is a schematic diagram showing the synthetic pathway to 87.1-mimic (16).

FIG. 6 is a schematic diagram showing the synthetic pathway to CD4–1 mimic (22).

FIG. 7 is a graph showing concentration-dependent inhibition of CD4 by structure (22).

DETAILED DESCRIPTION OF THE INVENTION

It has been found in accordance with the present invention that non-peptide compounds which are immunologically crossreactive with antibodies can be produced through careful structural analysis of at least one complementarity determining region (CDR) of the antibody. It will be recognized that immunologically crossreactive moieties are those which exhibit substantially identical activity in at least one of the many immunological binding phenomena known in the art such as, for example, antigen, antibody, receptor, and cell surface binding. There exist a wide variety of useful analytical techniques for determining the precise structure of antibody CDRs, including amino acid sequencing, x-ray crystallography, nuclear magnetic resonance spectroscopy, computer-assisted molecular modeling, peptide mapping, site-directed mutagenesis, and combinations thereof. Representative applications of these techniques to CDR structural elucidation are provided by Williams, et al., Proc. Natl. Acad. Sci. USA, 1989, 86, 5537; Williams, et al., Proc. Natl. Acad. Sci. USA, 1988, 85, 6488; and Taub, et al., J. Biol. Chem., 1989, 264, 259.

Structural analysis of an antibody CDR generally provides a large body of data which in preferred embodiments comprises the amino acid sequence of the CDR as well as the three-dimensional positioning of its atomic components. It is believed that only certain of these components, which are known both individually and collectively as chemical functionality, participate in any given immunological binding phenomena. It will be appreciated that the participation of a chemical functional group in immunological binding is manifested by the linkage of the functional group with at least a portion of a bound moiety such as an antigen or a cellular receptor. Such linkage may be effected through a covalent or ionic bond or some weaker atomic coordination effect such as complexation or crystallization.

In accordance with the present invention, CDR chemical functionality which participates in immunological binding is identified by a stepwise process wherein one or more variant peptides are prepared by amino acid substitution at one or more positions of the CDR sequence. The activity of the variant peptides in the binding event of interest is then compared with that of the CDR. The degree to which the activity of the variant peptide corresponds with that of the CDR indicates the participation of the individual CDR amino acids—and, more importantly, their component chemical functionality—in the binding phenomena. Accordingly, one important criteria in preparing variant peptides is the respective chemical similarity of the individual amino acids found in the CDR and any potential substitutes therefor in the variant peptides. In general, it is desired that a CDR amino acid and its substitute in the variant peptide be chemically dissimilar. Where the substitute is chemically dissimilar from the CDR amino acid, it will generally be easier to elucidate the contribution, if any, of CDR chemical functionality to antibody and/or CDR activity. For example, in studying the role of specific amino acid residues in the interaction of the mAb 87.92.6 light chain variable region ($V_L$) with the reovirus type 3 receptor, Williams, et al. employed variant peptides with substitutions at several positions in the putative binding domain of the $V_L$. Their studies indicated that deletion of hydroxyl groups from positions 11 (tyrosine), 12 (serine), 14 (serine), or 15 (threonine) reduced the apparent affinity of these peptides for the reovirus type 3 receptor on some cells. Thus, for the interaction of the mAb 87.92.6 light chain variable region with the reovirus type 3 receptor, hydroxyl groups appear to be participatory CDR chemical functionality.

The present invention, however, is not limited to embodiments wherein hydroxyl groups participate in binding. Participatory chemical functionality according to the present invention includes any of the wide variety of functional groups known in the art. The side chains of naturally-occurring amino acids are preferred. Representative participatory CDR chemical functionality is set forth in Table 1.

TABLE 1

| | |
|---|---|
| $CH_3-$ | $CH_3-CH_2-S-CH_2-CH_2-HO-CH_2-CH_2-$ |
| $HO-CH_2-$ | $CH_3-CH_2(OH)-$ |
| $C_6H_5-CH_2-$ | $HO_2C-CH_2-NH_2C(O)-CH_2-$ |
| $HO-C_6H_5-CH_2-$ | |
| (dihydroxyphenyl-CH$_2$–) | (pyrrolidine structure) |
| (indole-CH$_2$–) | $HCO_2-CH_2-CH_2-$ |
| | $NH_2C(O)-CH_2-CH_2-$ |
| | $(CH_3)_2-CH-$ |
| | $(CH_3)_2-CH-CH_2-$ |
| | $CH_3-CH_2-CH_2-$ |
| | $H_2N-CH_2-CH_2-CH_2-$ |
| (imidazole-CH$_2$–) | $H_2N-C(NH)-NH-CH_2-CH_2-CH_2-$ |
| | $H_2N-C(O)-NH-CH_2-CH_2-CH_2-$ |
| | $CH_3-CH_2-CH(CH_3)-$ |
| | $CH_3-CH_2-CH_2-CH_2-$ |
| $HS-CH_2-$ | $H_2N-CH_3-CH_2-CH_2-CH_2-$ |
| $HO_2C-CH(NH_2)-CH_2-S-S-CH_2-$ | |
| $CH_3-CH_2-$ | |
| $CH_3-S-CH_2-CH_2-$ | |

After participatory CDR chemical functionality has been identified, the three-dimensional positioning of that functionality is determined by known techniques such as, for example, x-ray crystallography, nuclear magnetic resonance spectroscopy, and computer-assisted molecular modeling. For example, Williams, et al., employed a comparative modeling approach to generate a three-dimensional molecular model of the 87.92.6 $V_L$ showing the precise positions of the hydroxyl groups implicated in binding the reovirus type 3 receptor.

A synthetic compound which is immunologically crossreactive with the CDR is next prepared by synthetically appending the identified chemical functionality to a core molecule having a conformation which approximates that of the CDR β-turn. The synthetic compound should comprise the identified functionality in amount effective to render it immunologically crossreactive with the CDR. The compound also should exist in at least one conformation which is substantially identical to the conformation assumed by the CDR during the binding phenomena of interest. In preferred embodiments, the synthetic compound also exhibits good chemical stability under a variety of conditions, especially those encountered in the human body.

While any synthetic compound meeting the above criteria may be employed, preferred molecules have been found to possess the general structure (2):

(2)

(5)

(6)

wherein $R_1$, $R_2$, and $R_3$ are chemical functional groups which comprise the CDR chemical functionality identified to participate in binding. The cyclic portion of structure (2) is a preferred mimic of the CDR $\beta$-turn. Preferred synthetic compounds—which have been found to be immunologically crossreactive with the second complementarity region of the 87.92.6 $V_L$—are those wherein $R_1$, $R_2$, and $R_3$ comprise at least one hydroxyl group. Preferably, $R_1$ and $R_2$ individually comprise one hydroxyl group and $R_3$ comprises two hydroxyl groups Preferably $R_1$ is —$CH_2OH$ $R_2$ has the structure (3) wherein $R_{2A}$ is a chemical functional group, and $R_3$ has the structure (4) wherein $R_{3A}$ and $R_{3B}$ are each chemical functional groups comprising one hydroxyl group.

(3)

(4)

More preferably, $R_{2A}$ has the structure (5) and $R_3$ has the structure (6). Particularly preferred synthetic compounds according to the present invention are those having the structure (1), as well as salts having structure (16), below.

As can be seen, the present invention provides methods for the preparation of synthetic compounds which are immunologically crossreactive with individual antibody CDRs. The invention also provides compositions which comprise one or more of these synthetic compounds. To the extent that the compositions comprise synthetic compounds which are immunologically crossreactive with antibody CDRs, the compositions likely will be immunologically crossreactive with the antibodies themselves. It will be appreciated that where but a single antibody CDR participates in a particular binding phenomena, compositions which are immunologically crossreactive with the antibody need only comprise the synthetic compound which is immunologically crossreactive with that particular CDR. In addition to the synthetic compounds of the present invention, the compositions may further comprise binders, carriers, flow agents, or any other inert material.

The synthetic compounds may be present in the compositions in any of a wide variety of forms. For example, two or more compounds may be merely mixed together or may De more closely associated through complexation, crystallization, or ionic or covalent bonding. It is preferred that two or more synthetic compounds be covalently bound when present in compositions of the invention. Such covalent binding can be effected by any of the many techniques known in the art. Preferably, covalent binding does not diminish the individually crossreactivity of the bound synthetic compounds. One exemplary composition comprising covalently bound compounds is given by structure (7).

(7)

Those skilled in the art will appreciate that a wide variety of prophylactic, diagnostic, and therapeutic treatments may be prepared from the synthetic compounds and compositions of the invention, due in large part to the immunological crossreactivity of these moieties with one or more antibody CDRs. For example, by administering an effective amount of a composition comprising a synthetic compound which is immunologically crossreactive with an antibody CDR, prophylactic or therapeutic responses can be produced in a human or some other type mammal. It will be appreciated that the production of prophylactic or therapeutic responses includes the initiation or enhancement of desirable responses, as well as the cessation or suppression of undesirable responses.

Additional objects, advantages, and novel features of this invention will become apparent to those skilled in the art upon examination of the following examples thereof, which are not intended to be limiting.

EXAMPLE 1

As outlined in FIG. 4, D-aspartic acid dimethyl ester hydrochloride (2.00 grams, 10.1 millimoles), t-butyl-dimethyl-silylchloride (1.68 grams, 11.1 millimoles) and 4-dimethyl-aminopyridine (62 milligrams, 0.51 millimoles) were dissolved in 50 milliliters of methylene chloride. To this mixture was added triethylamine (3.24 milliliters, 23.3 millimoles) at room temperature slowly and the mixture was allowed to stir for about 12 hours at room temperature. The mixture was washed with aqueous ammonium chloride, saturated sodium bicarbonate and brine, dried over sodium sulfate and concentrated in vacuo. The residue was dissolved in 50 milliliters of diethyl ether. The solution was cooled to 0° C. and 2.0 molar t-butylmagnesium chloride in diethyl ether (5..24 milliliters, 10.5 millimoles) was added dropwise. The mixture was allowed to warm to room temperature for about 12 hours with stirring and was cooled to 0° C. again. Saturated ammonium chloride was added and the mixture was stirred for 30minutes. Water was added to the mixture and the organic layer was separated. The aqueous layer was extracted with diethyl ether (2×30 milliliters). The combined organic extracts were washed with brine, dried over magnesium sulfate and concentrated in vacuo. The residue was dissolved in 60 milliliters of methanol. To this solution at room temperature, sodium borohydride (1.14 grams, 30.1 millimoles) was added to a flask equipped with a reflux condenser. The mixture began to reflux during the addition and ceased after 20 minutes. After 45 minutes in total the mixture was cooled to 0° C. and aqueous ammonium chloride was added. The mixture was extracted with methylene chloride (3×50 milliliters). The combined organic extracts were dried over sodium sulfate and the volatiles were removed in vacuo. The residue was dissolved in 30 milliliters of methylene chloride. To this solution was added t-butyl-dimethylsilyl chloride (1.00 grams, 6.64 millimoles) and 4-dimethylamino--pyridine (37 milligrams, 0.30 millimoles). Triethylamine (1.10 milliliters, 7.87 millimoles) was added slowly and the mixture was allowed to stir for about 12 hours at room temperature. The mixture was washed with aqueous ammonium chloride and brine, dried over sodium sulfate and concentrated in vacuo.

Flash chromatography of the residue on silica gel with hexane/ethyl acetate (9/1 on a volume basis) afforded 1.01 grams (30%) of the azetidinone having structure (s) as colorless liquid. $^1H$ NMR (400 MHz $CDCl_3$): delta 3.74 (dd $J_a$=3.96 HZ , $J_b$=10.30 HZ, 1H) 3.63 (dd, $J_a$=5.12 HZ , $J_b$1=10.30 HZ, 1H) , 3.59 (m, 1H), 3.04 (dd, $J_b$=5.28 Hz, $J_b$=15.22 Hz, 1H), 2.76 (dd, $J_a$=2.49 HZ, $J_b$=15.22 HZ, 1H) , 0.94 (s, 9H) , 0.88 (s, 9H) , 0.22 (s, 3H) , 0.21 (s, 3H) , 0.05 (S,6H); $^{13}C$ NMR (100 MHz, $CDCl_3$): delta 172.7, 65.3, 50.2, 41.2, 26.2, 25.8, −5.4, −5.5, −5.7.

A solution of lithium diisopropyl amide (2.Smillimoles in 25 milliliters of THF) was prepared and cooled to −78° C. A solution of azetidinone (7) (323 milligrams, 1 millimole) in 10 milliliters of tetrahydrofuran (THF) was added dropwise and allowed to stir for 30 minutes at −78° C. To this was added 400 milliliters (4 millimoles) of butenyl bromide. Stirring was continued for 18 hours and the reaction allowed to come to room temperature- The reaction mixture was poured into saturated $NH_4Cl$ solution and extracted 3 times with 50 milliliters portions of diethyl ether, dried over $Na_2SO_4$ and the solvent removed in vacuo. The residue was chromatographed on 15 grams of silica gel to provide 294 milligrams (78%) of the azetidinone having structure (9) (TBDMS=tributyldimethylsilyl).

A flask was charged with a magnetic stirrer, 4 milliliters $CCl_4/CH_3CN/H_2O$ (1:1:2), azetidinone (8) (160 milligrams, 0.44 millimoles) and $NaIO_4$ (469 milligrams, 2.2 millimoles, 5 equivalents) . To this biphasic solution, a catalytic amount of $RuCl_3 \cdot 3H_2O$ was added. The mixture was stirred for about 12 hours at room temperature and taken up in ethyl acetate (25 milliliters) and $H_2O$ (10 milliliters). The organic layer was separated and the aqueous layer was saturated with sodium chloride (solid) and extracted with ethyl acetate (2×20 milliliters). The combined organic extracts were dried over $Na_2SO_4$ and concentrated to provide the azetidinone having structure ( 10 ) as an oil in 55–65% yield.

EXAMPLE 2

The serine derivative having structure (11) (Z=carbobenzoxy, 0.4 millimoles, 143 milligrams) was prepared according to the procedure set forth by Hoffmann, Tetrahedron Lett., 1990, 31, 2753 and was dissolved in 5 milliliters of anhydrous tetrahydrofuran (THF) along with the compound having structure (12) (FMOC = fluorinated methoxycarbonyl, 220 milligrams, 0.53 millimoles), which was prepared according to the procedure of Fuller, et al., J. Amer. Chem. Soc., 1991, 112, 7414. The reaction mixture was stirred at room temperature for about 18 hours and then diluted with 15 milliliters of $CH_2Cl_2$, after which 5 milliliters of saturated $NaHCO_3$ solution was added. The organic layer was separated and the aqueous layer washed with 2×10 milliliters of $CH_2Cl_2$. The combined organic extracts were dried over $Na_2SO_4$ and the volatiles removed in vacuo. Flash chromatography on $SiO_2$ using $CH_2Cl_2$:$CH_3OH$ (100:1) as the eluent provided 94 milligrams (32%) of the dipeptide. The dipeptide was dissolved in 5 milliliters of anhydrous $CH_2Cl_2$ and 50 microliters of piperidine added. The reaction was allowed to stir for 10 hours under inert atmosphere. Removal of the volatiles in vacuo provided structure (13), which was used without further purification.

Coupling of structure (13) (0.12 millimoles) with the azetidinone having structure (10) (0.15 millimoles, 59 milligrams) was effected by formation of the mixed anhydride of structure (10) by treatment with isobutylchloroformate (0.15 millimoles, 19.4 microliters) and N-methylmorpholine (0.15 millimoles, 16.5 microliters), followed by stirring in anhydrous THF at room temperature for 16 hours. Flash chromatography on silica gel with $CH_2Cl_2:CH_3OH$ (50:1) as eluent afforded structure (14) (92 milligrams, 82%).

Hydrogenolysis of structure (14) (86 milligrams, 0.09 millimoles) in 4 milliliters of $CH_3OH$ under 1 atmosphere of hydrogen gas with a catalytic amount of 10% palladium on carbon catalyst for 16 hours at room temperature afforded structure (15) (74 milligrams, 0.086 millimoles) after filtration and removal of volatiles in vacuo.

The mixed anhydride of N-carbobenzoxytyrosine was prepared by treatment with isobutylchloroformate (0.1 millimoles, 13.4 microliters) and N-methylmorpholine (0.1 millimoles, 10.8 microliters). The mixed anhydride (31.5 milligrams, 0.1 millimoles) was then coupled with structure (15) (50 milligrams, 0,062 millimoles) in 2 milliliters $THF:CH_2Cl_2$ (1:1) for 16 hours at room temperature under inert atmosphere afforded a fully protected analog of structure (16). $^1H$ NMR (400 MHz, $CDCl_3$): delta 0.03 (s, 6H) , 0.18 (s, 3H), 0.22 (s, 3H), 1.45–1.63 (m, 6H), 1.98–2.10 (m, 2H), 2.40–2.63 (m, 2H), 2.88–3.13 (m, 3H), 3.15–4.05 (m, 8H), 4.38–4.67 (m, 5H) , 5.02–5.28 (m, 5H) , 6.67 (d, 2H) , 7.02 (d, 2H) , 7.30 (m, 15H).

Hydrogenolysis in methanol saturated with HCl gas afforded structure (16) as its the hydrochloride salt. Final purification was effected using reverse phase C18 high performance liquid chromatography with a gradient of 0% to 70% $CH_3CN$ and 0.05% trifluoroacectic acid at a flow rate of 3 milliliters/minute.

EXAMPLE 3

Williams, et al. have shown that the mouse IgG mAb 9BG5 efficiently binds the intact mouse IgM 87.92.6 or the 17 amino acid peptide analogs VL and VLA5 derived from the 87.92.6 mAb second CDR. Also, Kieber-Emmons, et al., Int. Rev. Immunol., 1987, 2, 339 disclosed that 9BG5mAb binds the dimeric VL form VLSH but not the 15 amino acid peptide analog 1S1 derived from the Reovirus Type 1 sigma-1 protein sequence.

The 87.1-mimic prepared in Example 2 was tested for its ability to directly bind the mouse IgG 9BG5 mAb idiotype in a solid phase radioimmunoassay by coupling 2.5 micrograms of the 87.1-mimic in 50 microliters deuterated water to polypropylene microtiter plates by evaporation for about 8 hours at 37° C. The unreacted sites on the plates were blocked by washing the plates three times for 10 minutes each with a binding buffer (Hank's balanced saline solution (HBSS), 1.5 percent bovine serum albumin (BSA), and 0.005 percent sodium azide) and then incubating the plates with 5 micrograms of Protein A purified 9BG5 mAb in 50 microliters of binding buffer for 2 hours at room temperature.

After three flushes with binding buffer, 0.05 microcuries (about 70,000 counts per minute/well) of $^{125}$I-goat anti-mouse IgG was added in 50 microliters of binding buffer, incubated for 40 minutes at room temperature and then flushed 3 times in binding buffer.

Figure 1:
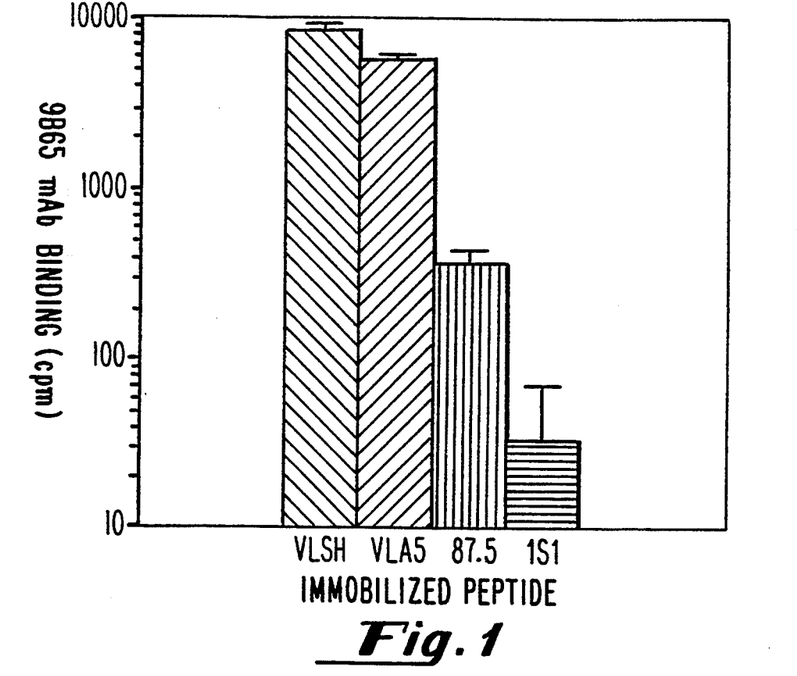

The bound complexes were removed from the plates by washing with deuterated water containing 1.5 percent sodium dodecyl sulfonate (SDS) and counted in a Gamma Counter. The average background counts per minute (cpm) of the plates without peptides or with isotype matched irrelevant mAb was 101 cpm and was subtracted from the data shown in FIG. 1. As can be seen from FIG. 1, specific binding of the 87.1-mimic to the 9BG5mAb occurred. Binding was approximately 14 times that for the 1S1 negative control peptide, whereas both the VLSH and the VLA5 positive control cyclic analog peptides bound the 9BG5 mAb.

Figure 2:
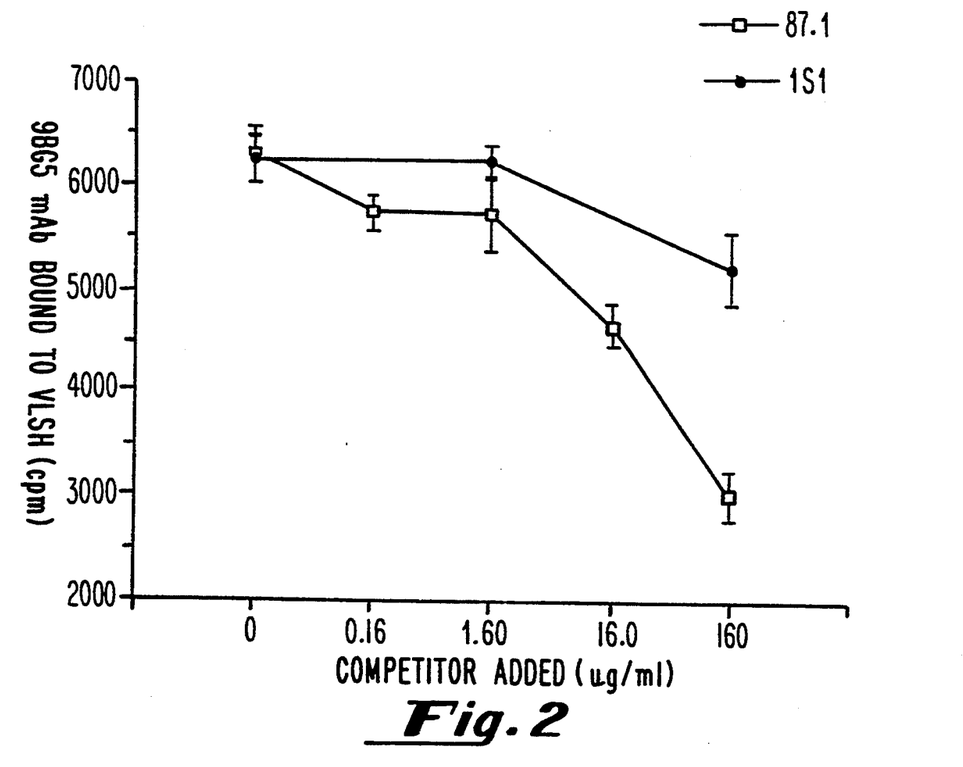

The ability of the soluble 87.1-mimic to bind the 9BG5 mAb was next tested using the same procedure, except that the 9BG5 mAb was pre-incubated for 2 hours at room temperature with the soluble 87.1-mimic or the 1S1 control and then contacted with immobilized VLSH on radio immunoassay plates. As shown in FIG. 2, incubation with 87.1-mimic appears to have competitively inhibited 9BG5 mAb binding to solid phase VLSH. The competition by the 87.1-mimic was dose dependent. An estimated 70 to 700 fold molar excess of the 87.1-mimic over 9BG5 mAb was required for an inhibition of binding to VLSH ranging from about 20 to about 50 percent, respectively.

Taken together, these results indicate that the 87.1-mimic binds to the 9BG5mAb both in a solid and a liquid phase and this is immunologically crossreactive with 87.92.6 mAb.

EXAMPLE 4

The peptides VLA5 and VLSH and the intact 87.92.6 mAb interact with the cell surface receptor for Reovirus Type 3 and that this binding leads to an arrest of mitogen-induced DNA synthesis in T cell. In order to further evaluate whether the 87.1-mimic of Example 2 reproduced the biological activity of the intact mAb, the inhibitory effects of the mimic on cells bearing the Reovirus Type 3 receptor were assayed. Concanavalin A (ConA) T cells were prepared by incubating splenocytes taken from a Balb/c mouse with 5 microgram/milliliter ConA in 96 well microtiter plates at $5.0 \times 10^5$ cells/well for about 40 hours to induce the expression of the Reovirus Type 3 receptor. Antibodies, peptide analogs, or the 87.1-mimic were then added at the concentrations indicated in FIG. 3 and the plates were incubated for an additional 16 hours. The plates were then pulsed with 1.0 microcuries/well $^3$H-Thymidine for 4–6 hours and then harvested. The incorporated cpm were counted in a Beta Counter using Econofluor scintillation fluid, which is available from New England Nuclear, Boston, Ma. The wells to which no inhibitor was added incorporated 21,164±5,525 cpm and wells to which no ConA was added incorporated 699±627 cpm.

Figure 3:
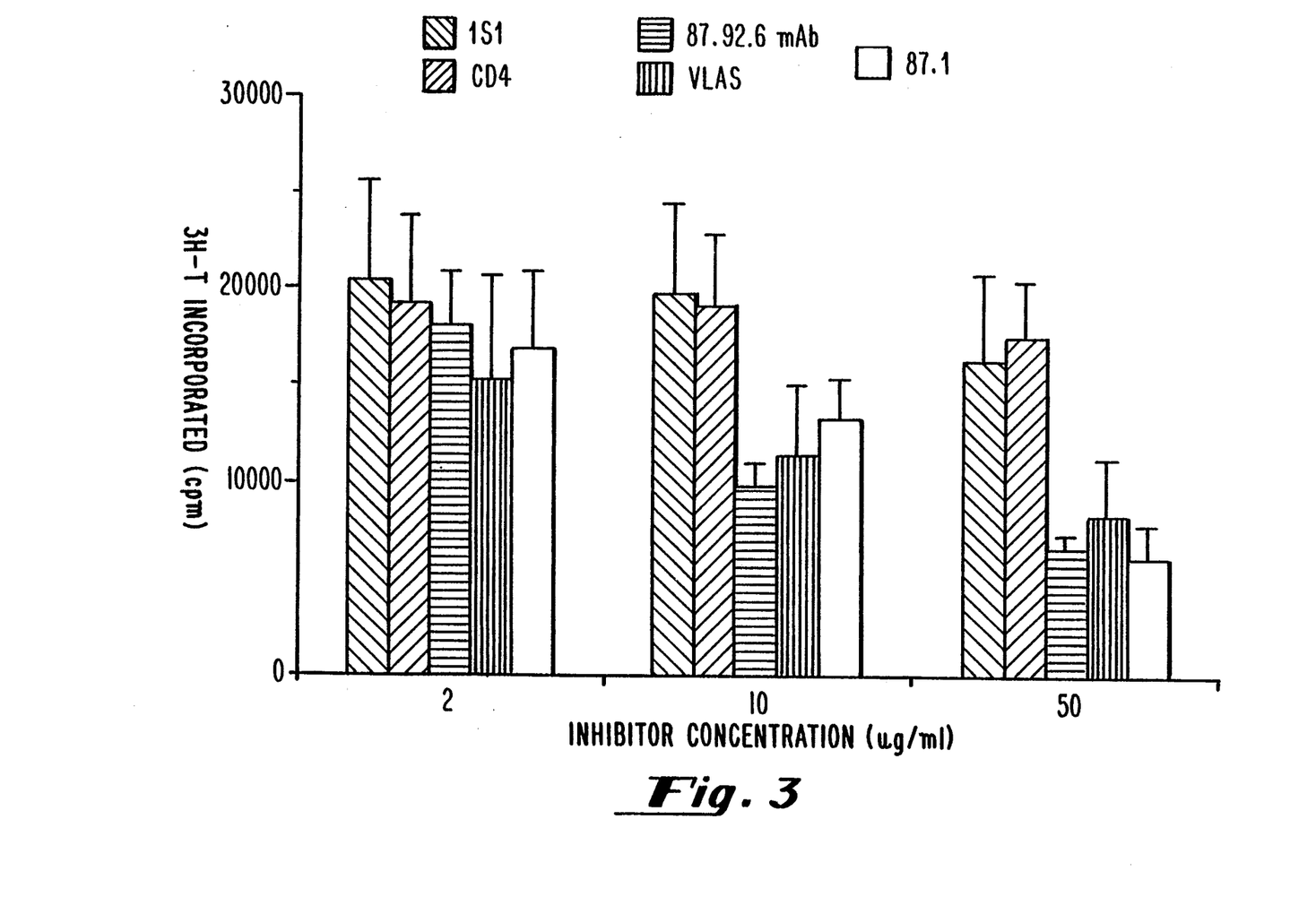
Figure 4:
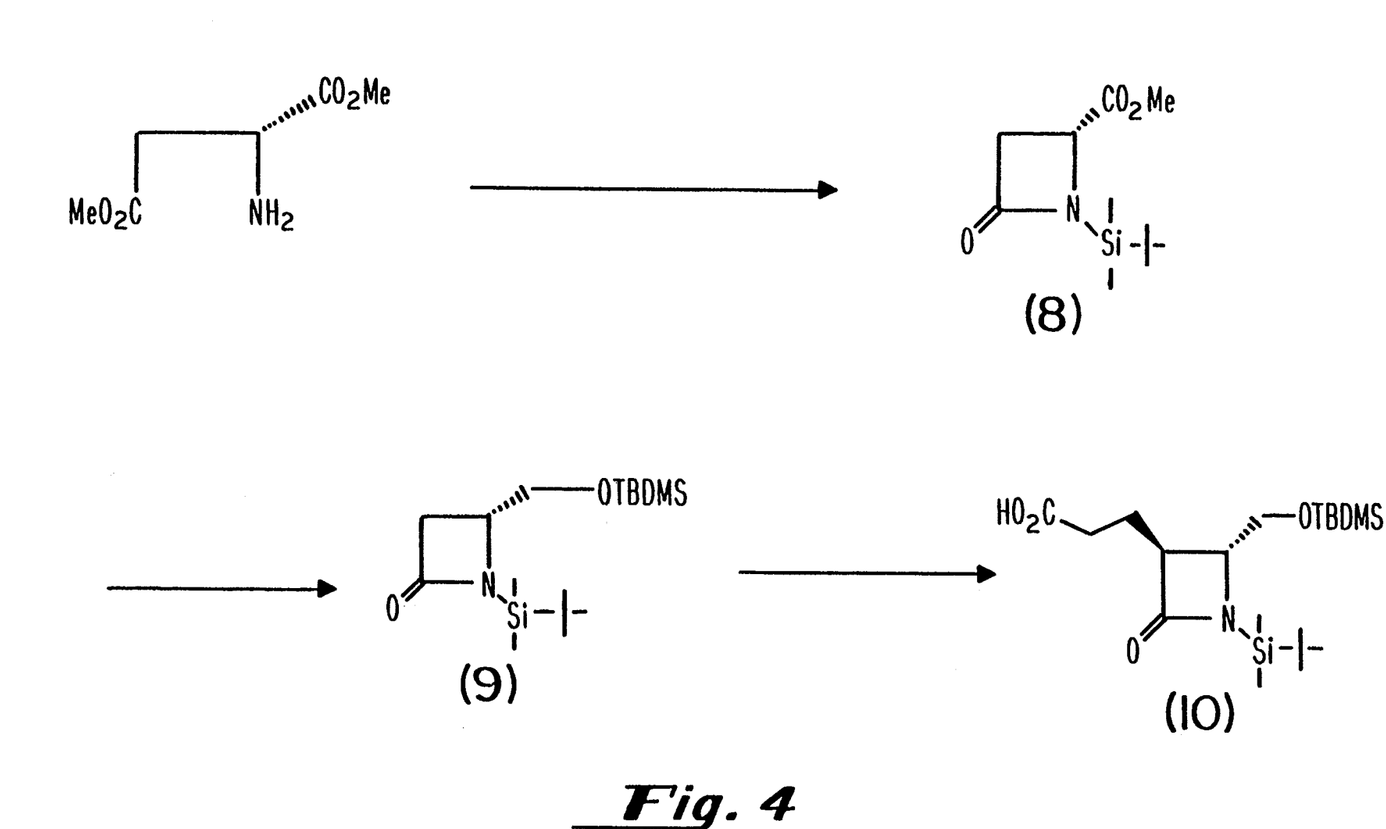
Figure 5A:
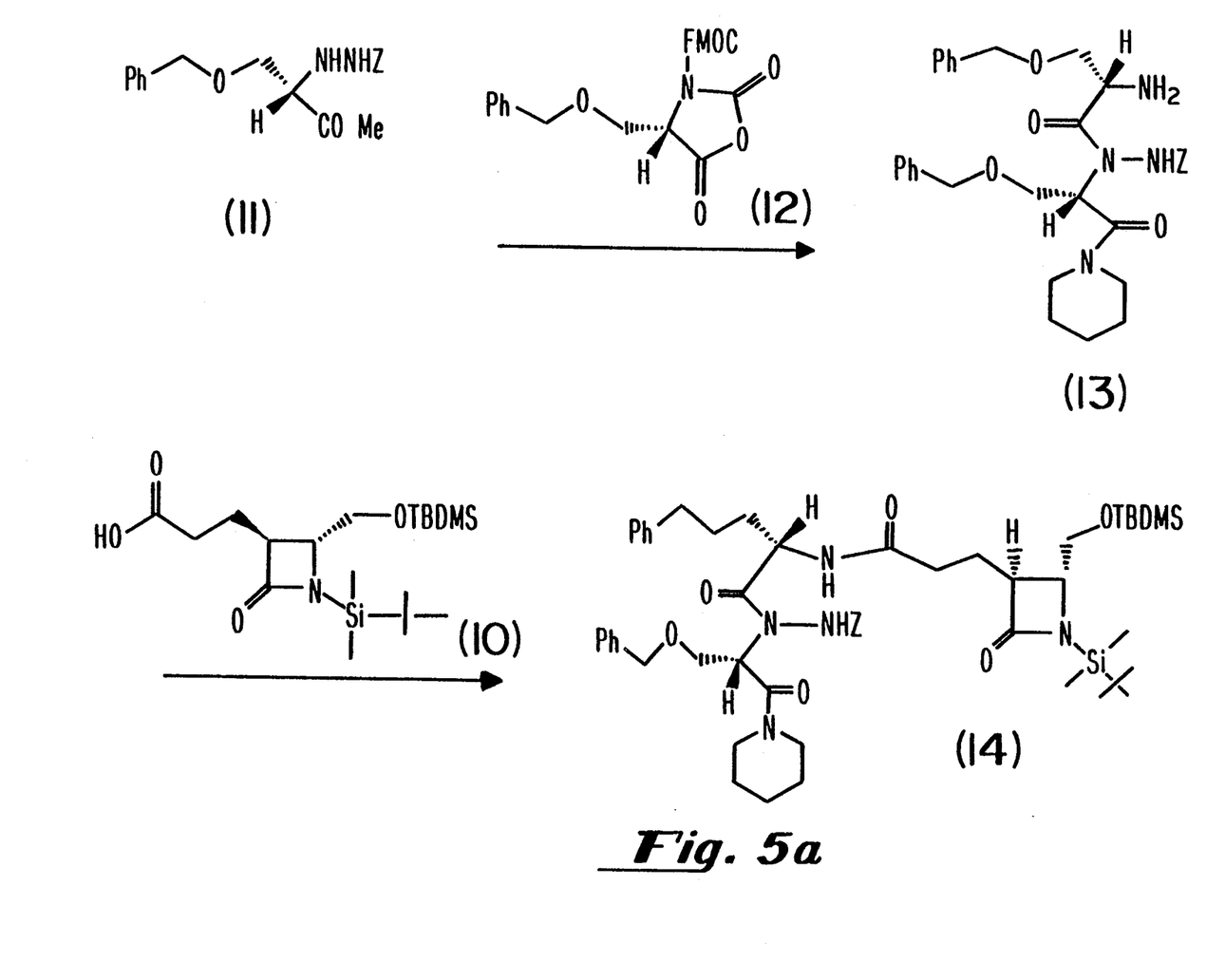
Figure 5B:
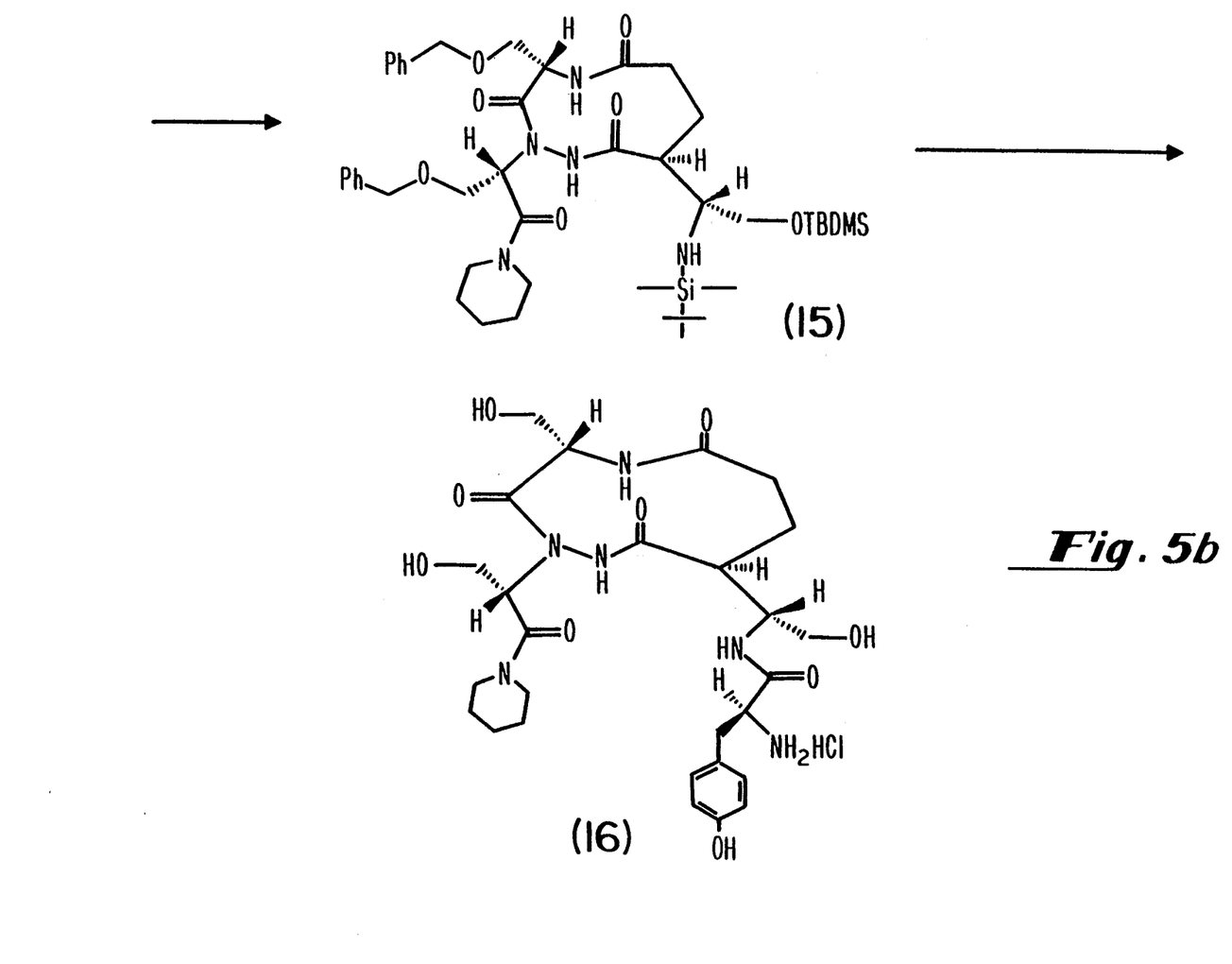
Figure 6:
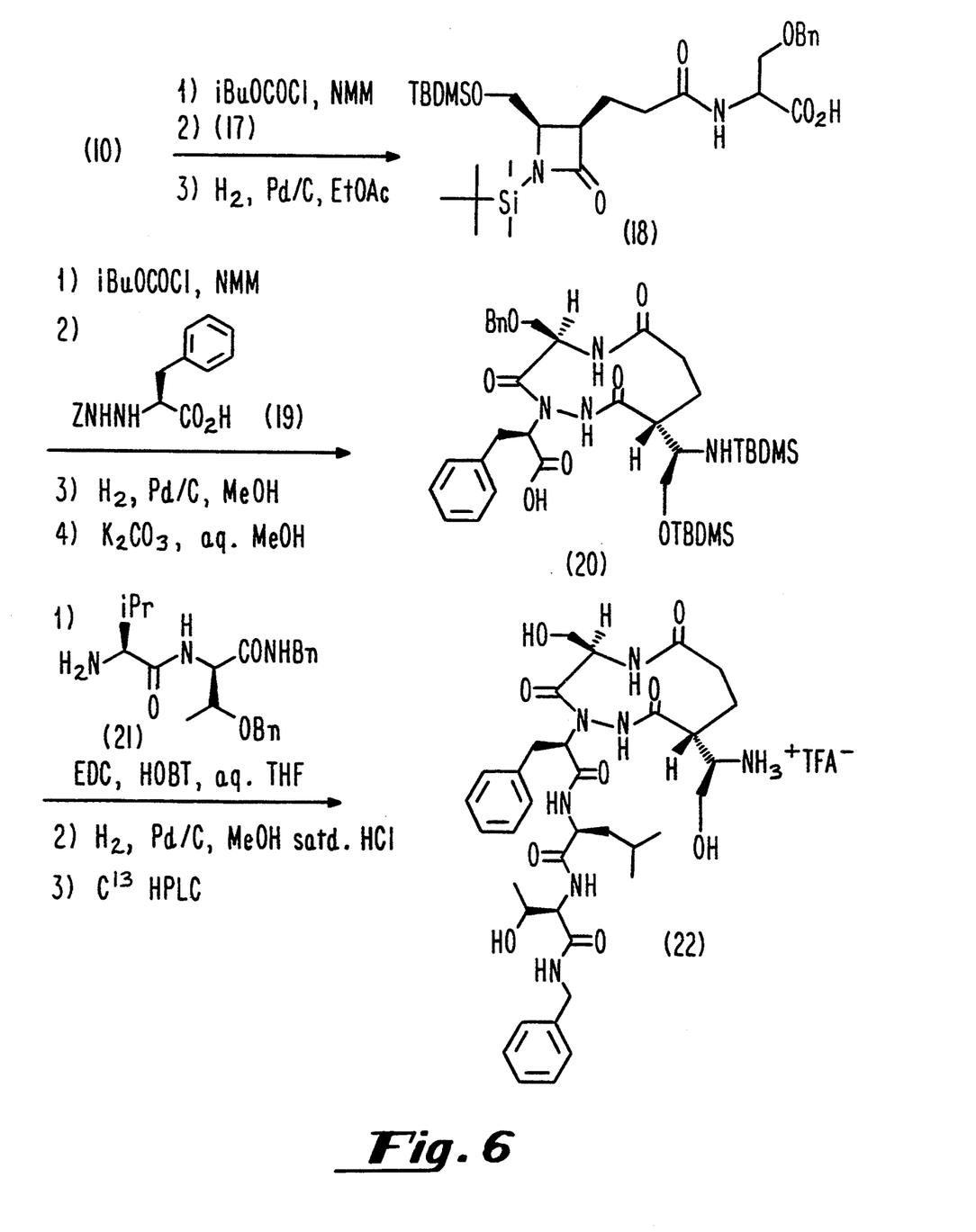

As shown in FIG. 3, the 87.1-mimic inhibited ConA-induced T cell proliferation in dose dependent fashion, as did the VLA5 and the intact 87.92.6 mAb. The 1S1 peptide analog was set up as a negative control, as was a compound derived from residues 41–54 of the human cell surface antigen CD4. The compound was selected to mimic a $\beta$-turn. As can be seen, these controls had no effect on the mitogenic response. In addition, high doses of the 87.1-mimic had no effect on the proliferation of SV40 transformed mouse fibroblast cells that lack the Reovirus Type 3 receptor and do not bind the 87.92.6 mAb, yet inhibited the proliferation of Ri.1 mouse thymoma cells that express the Reovirus Type 3 receptor and bind the 87.92.6 mAb.

These tests collectively suggest that the inhibitory effects are mediated through binding to the Reovirus Type 3 receptor. The concentrations of inhibitor required for 50 percent inhibition were extrapolated from FIG. 3. The estimated concentration of intact 87.92.6 mAb was 15–20 nanomolar. Although the 87.1-mimic required a 55–70 micromolar concentration, nearly 3 logarithmic units higher than the intact mAb, the properties of the 87.1-mimic are structurally and functionally analogous to the 87.92.6 mAb. Accordingly, the 87.1-mimic and the 87.92.6 mAb are immunologically cross-reactive according to the present invention.

EXAMPLE 5

Azetidinone (10) was prepared in six steps (22% yield from dimethylaspartate by a procedure generally in accordance with Saltzmann, et. al., J. Am. Chem. Soc., 1980, 102, 6161 and Williams, et al., J. Am. Chem. Soc., 1989, 111, 1073. Mixed anhydride coupling of (10) to O-benzyl serine benzyl ester (17) and subsequent hydrogenolytic cleavage of the benzyl ester provided acid (18) in 88% yield. Coupling of Z-protected phenylalanine hydrazide (19), reductive closure, and saponification afforded structure (20). Dipeptide (21) was coupled to structure (20) using an aqueous carbodiimide protocol. Hydrogenolytic deprotection and purification by reverse phase HPLC provided homogeneous material which was characterized by 400 MHz NMR and PDMS as containing structure (22).

EXAMPLE 6

CD4 is a glycoprotein found on the surface of T lymphocytes. During human immunodeficiency virus (HIV) infection in humans, CD4 is the receptor for the gp120 envelope glycoprotein of HIV.

Figure 7:
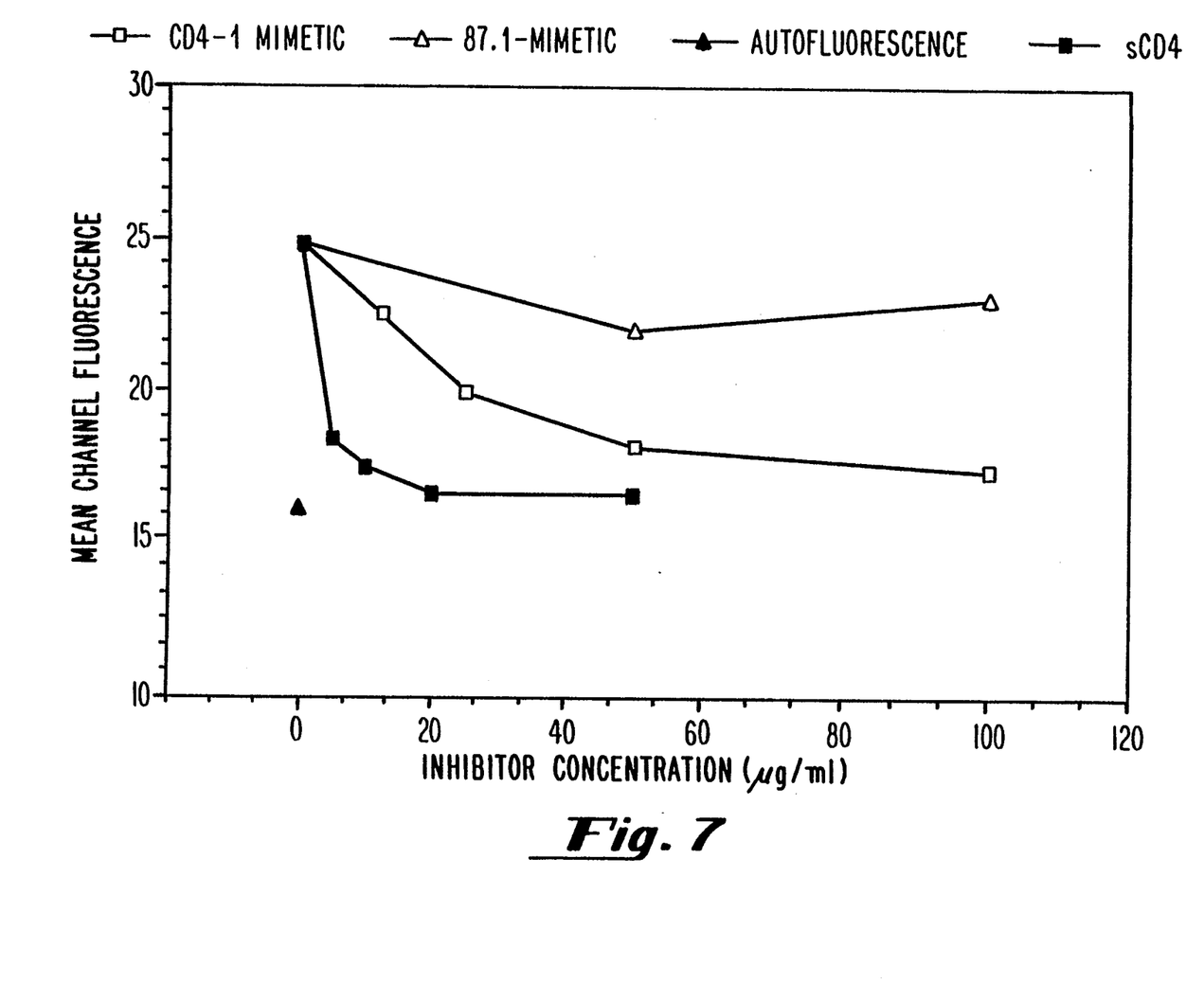

To assess the ability of structure (22) to inhibit gp120 binding, fluorescinated gp120 was incubated with structure (22) or with soluble CD4 at 22° C. in a binding buffer containing $Ca^{2+}$, $Mg^{2+}$, free Hank's balanced saline solution (HBSS), 0.5% bovine serum albumin (BSA), and 0.05% sodium aziode at pH 7.4. Approximately 300,000 CD4-expressing cells (from a $10 \times 10^7$ cell/ml stock) were added to tubes at 4° C. in the binding buffer, with a final volume of 100 microliters. Samples were incubated at 4° C. for 40 minutes, washed in binding buffer, and immediately analyzed in a fluorescence activated cell sorter (FACS). Data were acquired, gating on live cell populations (always greater than 90%). The results are shown in FIG. 7, which shows that inhibition by structure (22) CD4-1 Mimetic) was concentration dependent, with an $IC_{50}$ of 0.8 micromolar.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having the structure: